(12) United States Patent
Bandyopadhyay et al.

(10) Patent No.: US 11,304,663 B2
(45) Date of Patent: Apr. 19, 2022

(54) SYSTEMS AND METHODS FOR DETECTING ANOMALY IN A CARDIOVASCULAR SIGNAL USING HIERARCHICAL EXTREMAS AND REPETITIONS

(71) Applicant: Tata Consultancy Services Limited, Mumbai (IN)

(72) Inventors: Soma Bandyopadhyay, Kolkata (IN); Arijit Ukil, Kolkata (IN); Chetanya Puri, Kolkata (IN); Rituraj Singh, Kolkata (IN); Arpan Pal, Kolkata (IN); C A Murthy, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 391 days.

(21) Appl. No.: 16/230,053

(22) Filed: Dec. 21, 2018

(65) Prior Publication Data

US 2019/0200935 A1    Jul. 4, 2019

(30) Foreign Application Priority Data

Dec. 29, 2017 (IN) .............................. 201721047277

(51) Int. Cl.
  *A61B 5/00* (2006.01)
  *G06K 9/00* (2022.01)
  (Continued)

(52) U.S. Cl.
  CPC .......... *A61B 5/7264* (2013.01); *A61B 5/7203* (2013.01); *A61B 5/7221* (2013.01);
  (Continued)

(58) Field of Classification Search
  CPC ... A61B 5/7264; A61B 5/7203; A61B 5/7221; A61B 5/7282; A61B 5/02416;
  (Continued)

(56) References Cited

U.S. PATENT DOCUMENTS 6,024,705 A * 2/2000 Schlager .............. A61B 5/1102
                                                    600/508
7,324,848 B1   1/2008 Turcott
               (Continued)

FOREIGN PATENT DOCUMENTS

WO    WO-2009/063463    5/2009
WO    WO-2016/085768    6/2016

OTHER PUBLICATIONS

Liu, H. et al. (2015). "Toward a Smartphone Application for Estimation of Pulse Transit Time," *Sensors*, vol. 15; pp. 27303-27321.

(Continued)

*Primary Examiner* — Devin B Henson
*Assistant Examiner* — Justin Xu
(74) *Attorney, Agent, or Firm* — Finnegan, Henderson, Farabow, Garrett & Dunner LLP

(57) ABSTRACT

Systems and methods for detecting an anomaly in a cardiovascular signal using hierarchical extremas and repetitions. The traditional systems and methods provide for some anomaly detection in the cardiovascular signal but do not consider the discrete nature and strict rising and falling patterns of the cardiovascular signal and frequency in terms of hierarchical maxima points and minima points. Embodiments of the present disclosure provide for detecting the anomaly in the cardiovascular signal using hierarchical extremas and repetitions by smoothening the cardiovascular signal, deriving sets of hierarchical extremas using window detection, identifying signal patterns based upon the sets of hierarchical extremas, identifying repetitions in the signal patterns based upon occurrences and randomness of occurrences of the signal patterns and classifying the cardiovascular signal as anomalous and non-anomalous for detecting the anomaly in the cardiovascular signal.

11 Claims, 11 Drawing Sheets

(51) Int. Cl.
*G16H 50/20* (2018.01)
*G16H 50/30* (2018.01)
*A61B 5/318* (2021.01)
*G16H 50/70* (2018.01)
*A61B 5/024* (2006.01)

(52) U.S. Cl.
CPC ........ *A61B 5/7282* (2013.01); *G06K 9/00503* (2013.01); *G16H 50/20* (2018.01); *G16H 50/30* (2018.01); *G16H 50/70* (2018.01); *A61B 5/02416* (2013.01); *A61B 5/318* (2021.01)

(58) Field of Classification Search
CPC ...... A61B 5/0402; G16H 50/70; G16H 50/30; G16H 50/20; G06K 9/00503
See application file for complete search history.

(56) References Cited

U.S. PATENT DOCUMENTS

| | | | |
|---|---|---|---|
| 8,512,240 B1 | 8/2013 | Zuckerman-Stark et al. | |
| 9,339,202 B2 | 5/2016 | Brockway et al. | |
| 9,610,018 B2 | 4/2017 | Gulati et al. | |
| 2013/0218037 A1* | 8/2013 | Raeder | A61B 5/361 600/518 |
| 2015/0148696 A1 | 5/2015 | Lall et al. | |
| 2015/0282722 A1* | 10/2015 | Klepp | A61B 5/165 600/508 |
| 2015/0304101 A1 | 10/2015 | Gupta et al. | |
| 2017/0035308 A1 | 2/2017 | Gulati et al. | |
| 2017/0071546 A1 | 3/2017 | Jain et al. | |
| 2017/0071551 A1 | 3/2017 | Jain et al. | |

OTHER PUBLICATIONS

Malhotra, P. et al. "Long Short Term Memory Networks for Anomaly Detection in Time Series," *ESANN 2015 Proceedings of European Symposium on Artificial Neural Networks, Computational Intelligence and Machine Learning*, Bruges, Belgium, Apr. 22-24, 2015; 6 pages.

* cited by examiner

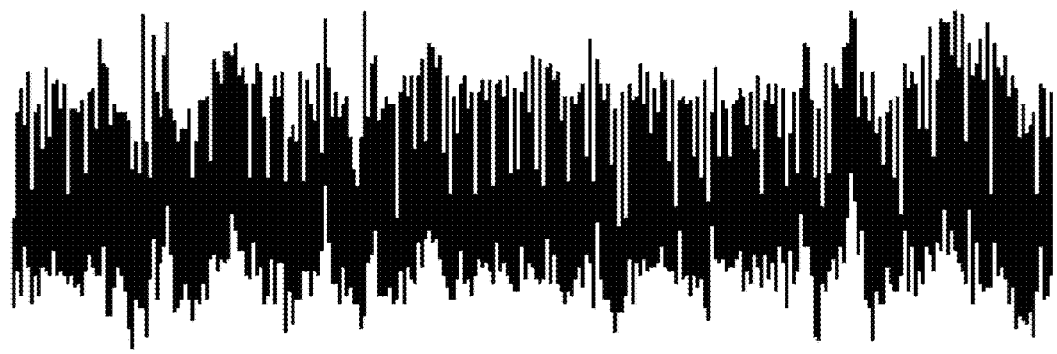
FIG. 9
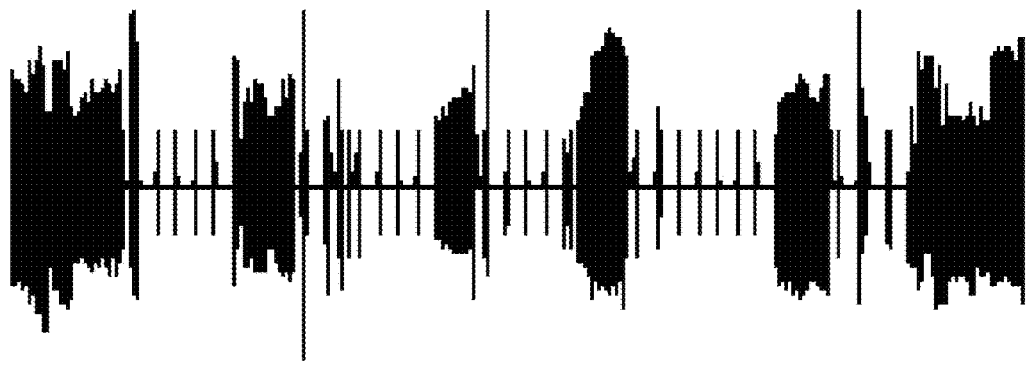
FIG. 10(a)
FIG. 10(b)

SYSTEMS AND METHODS FOR DETECTING ANOMALY IN A CARDIOVASCULAR SIGNAL USING HIERARCHICAL EXTREMAS AND REPETITIONS

PRIORITY CLAIM

This U.S. patent application claims priority under 35 U.S.C. § 119 to: India Application No. 201721047277, filed on Dec. 29, 2017. The entire contents of the aforementioned application are incorporated herein by reference.

TECHNICAL FIELD

The present disclosure generally relates to detecting an anomaly in a cardiovascular signal using hierarchical extremas and repetitions. More particularly, the present disclosure relates to systems and methods for detecting an anomaly in a cardiovascular signal using hierarchical extremas and repetitions

BACKGROUND

Cardiovascular signals such as arterial blood pressure (ABP), pulse oximetry (POX), and intracranial pressure (ICP) contain useful information such as heart rate, respiratory rate, and pulse pressure variation (PPV). The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

These cardiovascular signals like Electrocardiogram (ECG), Photoplethysmogram (PPG) signals impact considerably in the clinical decision process for the medical practitioners. Identification of patterns, particularly discriminating between normal and anomalous phenomena inside biomedical signal recordings, is one of the toughest problems in healthcare analytics. However, many signals corresponding to biological phenomena possess distinct patterns. Generally, in cardiovascular signals, repetitions occur in healthy individuals as well as in patients. It may also be noted that the signals are sometimes contaminated by noise, and consequently repetitions can occur in signals either with or without noise. Additionally, if the noise component is large, repetitions may not occur in such signals. On the other hand, many times we observe that patients with abnormality do not show strong repetitions in such signals even when there is no noise. These signals are generally observed in those cases where patient's health condition is unstable.

Biomedical signals generated from heart's activity, such as ECG, show repetitive behavior that captures hearts rhythm along with other cardiological aspects. Another cardiac signal, PPG measures the oxygen saturation in the blood non-invasively (for example from the fingertip) showing the variability in heart rate. The repeating cardiac cycle consists of the heart muscle's contraction known as systole and relaxation known as diastole manifested as peaks and troughs in the waveform respectively. These bio-medical signals carry vital information about the physiological condition of the heart. Further, ECG and other pulsating signals are gaining high importance to derive various physiological parameters. Hence extracting the various time series features of these signals and then co-relating them with physiological parameters is a necessity to obtain noninvasive, affordable healthcare analytics application. However, most of the time, the signals, for example, PPG, have a lot of noise, and analytics mostly run on low power/battery operated device like mobile phones.

Anomaly in the cardiac activity of a patient may be any deviation from the normal cardiac activity, for example, ventricular fibrillation, ventricular flutter, ventricular tachycardia and asystole. Anomalous phenomenon can occur either due to noise/faults in data measurement setting (e.g. loose apparatus, powerline interference, body movements, etc.) or due to some physiological abnormality. Anomalous electrical signals of a heart muscle are reflected by deviations in specific portions of the curve from the predicted norm. Anomaly detection in the biomedical signals therefore has increasingly become an important task among researchers and practitioners. For example, it may be used to detect any time periods of unusual ECG beats. The accuracy of the anomaly detection method directly reflects the result of the cardiac disease detection and diagnosis.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

Systems and methods of the present disclosure enable detecting an anomaly in a cardiovascular signal using hierarchical extremas and repetitions based on rise and fall and different amplitude values, for example, considering every local maxima point, the number of consecutively occurring previous points which are strictly rising and culminating at the local minima point. The embodiments of the present disclosure further considers the corresponding amplitude difference of that maxima point and the previous minima point. In an embodiment of the present disclosure, there is provided a method for detecting an anomaly in a cardiovascular signal using hierarchical extremas and repetitions, the method comprising: smoothening, using a filter, the cardiovascular signal acquired for filtering the cardiovascular signal; deriving, using a window detection technique, one or more sets of hierarchical extremas, based upon the smoothened cardiovascular signal, wherein the one or more sets of hierarchical extremas comprises maximum points and minimum points based on rising edges and falling edges of the cardiovascular signal, and wherein each level of hierarchy in the one or more sets of hierarchical extremas represents a different window size of detection; identifying, one or more elements of signal patterns, based upon the one or more sets of hierarchical extremas, wherein the one or more elements of signal patterns comprise multiple frequencies and significance associated with the cardiovascular signal for defining a plurality of physiological events of the user or noise; determining, occurrences and randomness of occurrences of the one or more elements of signal patterns, by computing an entropy of occurrences of the one or more elements of signal patterns, wherein the entropy comprises randomness of the one or more elements of signal patterns computed based upon probabilities of repetitions of the one or more elements of signal patterns and (ii) identifying, significance of repetitions of the one or more elements of signal patterns, based upon the occurrences and randomness of occurrences; determining the occurrences and randomness of occurrences of the one or more elements of signal patterns by obtaining one or more threshold values based upon an equi-probable occurrence of the one or more elements of signal patterns for classifying the one or more elements of signal patterns; identifying the significance of the one or more elements of signal patterns and the significance of repetitions by obtaining a lower triangular matrix based upon a hierarchy of extremas, wherein the lower triangular matrix comprises number of occurrences of the one or more elements of signal patterns to identify variability in the cardiovascular signal; identifying the significance of the one or more elements of signal patterns by evaluating entropy of elements of a lower triangular matrix based upon frequencies and number of points in the one or more elements of signal patterns to detect randomness of the one or more elements of signal patterns; detecting, one or more zero patterns in the cardiovascular signal based upon the one or more sets of hierarchical extremas and filtering, the one or more zero patterns, based upon a comparison of the one or more zero patterns and a predefined threshold for identifying the one or more elements of signal patterns; identifying the one or more elements of signal patterns further by identifying uni-modal and multi-modal patterns in the cardiovascular signal based upon the occurrences of the one or more elements of signal patterns and obtaining the one or more threshold values by computing an upper threshold value based upon occurrences and henceforth entropy of the one or more elements of signal patterns to detect the anomaly.

In an embodiment of the present disclosure, there is provided a system for detecting an anomaly in a cardiovascular signal using hierarchical extremas and repetitions, the system comprising one or more processors; one or more data storage devices operatively coupled to the one or more processors and configured to store instructions configured for execution by the one or more processors to: smoothen, using a filter, the cardiovascular signal acquired for filtering the cardiovascular signal; derive, using a window detection technique, one or more sets of hierarchical extremas, based upon the smoothened cardiovascular signal, wherein the one or more sets of hierarchical extremas comprises maximum points and minimum points based on rising edges and falling edges of the cardiovascular signal, and wherein each level of hierarchy in the one or more sets of hierarchical extremas represents a different window size of detection; identify, one or more elements of signal patterns, based upon the one or more sets of hierarchical extremas, wherein the one or more elements of signal patterns comprise multiple frequencies and significance associated with the cardiovascular signal for defining a plurality of physiological events of the user or noise; determine, occurrences and randomness of occurrences of the one or more elements of signal patterns, by computing an entropy of occurrences of the one or more elements of signal patterns, wherein the entropy comprises randomness of the one or more elements of signal patterns computed based upon probabilities of repetitions of the one or more elements of signal patterns and identify, significance of repetitions of the one or more elements of signal patterns, based upon the occurrences and randomness of occurrences to detect the anomaly in the cardiovascular signal; determine the occurrences and randomness of occurrences of the one or more elements of signal patterns by obtaining one or more threshold values based upon an equi-probable occurrence of the one or more elements of signal patterns to classify the one or more elements of signal patterns; identify the significance of the one or more elements of signal patterns and the significance of repetitions by obtaining a lower triangular matrix based upon a hierarchy of extremas, wherein the lower triangular matrix comprises number of occurrences of the one or more elements of signal patterns to identify variability in the cardiovascular signal; identify the significance of the one or more elements of signal patterns by evaluating entropy of elements of a lower triangular matrix based upon frequencies and number of points in the one or more elements of signal patterns to detect randomness of the one or more elements of signal patterns; detect, one or more zero patterns in the cardiovascular signal based upon the one or more sets of hierarchical extremas and filter, the one or more zero patterns, based upon a comparison of the one or more zero patterns and a predefined threshold for identifying the one or more elements of signal patterns; identify the one or more elements of signal patterns by identifying uni-modal and multi-modal patterns in the cardiovascular signal based upon the occurrences of the one or more elements of signal patterns; obtain the one or more threshold values by computing an upper threshold value based upon occurrences and henceforth entropy of the one or more elements of signal patterns to detect the anomaly.

It is to be understood that both the foregoing general description and the following detailed description are exemplary and explanatory only and are not restrictive of the invention, as claimed.

BRIEF DESCRIPTION OF THE DRAWINGS

The embodiments herein will be better understood from the following detailed description with reference to the drawings, in which:

FIG. 9 shows a lower triangular matrix generated to get a broader view of frequencies or repetitions of the one or more elements of signal patterns according to an embodiment of the present disclosure;

FIGS. 10(a) to 10(f) shows the graphical representation of examples of various waveforms taken randomly from data sets corresponding to the cardiovascular signal according to an embodiment of the present disclosure;

DETAILED DESCRIPTION

Figure 1:
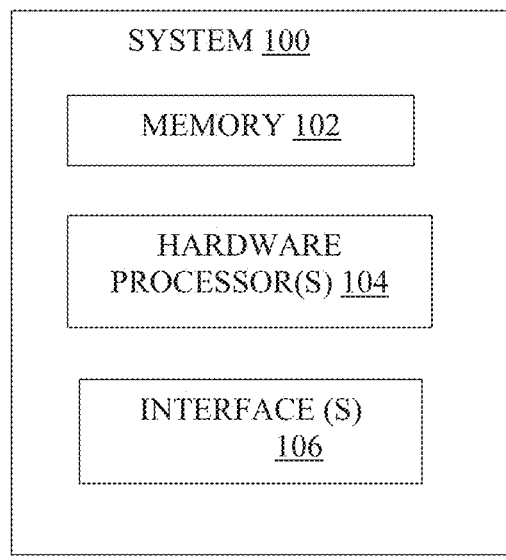
FIG. 1 illustrates a block diagram of a system for detecting an anomaly in a cardiovascular signal using hierarchical extremas and repetitions according to an embodiment of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments of the present disclosure provide systems and methods for detecting an anomaly in a cardiovascular signal using hierarchical extremas and repetitions. Cardiovascular signals such as arterial blood pressure (ABP), pulse oximetry (POX), and intracranial pressure (ICP) contain useful information such as heart rate, respiratory rate, and pulse pressure variation (PPV). The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

Generally, in a cardiovascular signal, repetitions occur in healthy individuals as well as in patients. It may also be noted that the signals are sometimes contaminated by noise, and consequently repetitions can occur in signals either with or without noise. Additionally, if the noise component is large, repetitions may not occur in such signals. On the other hand, many times we observe that patients with abnormality do not show strong repetitions in such signals even when there is no noise. These signals are generally observed in those cases where patient's health condition is unstable.

Anomalous phenomenon may occur either due to noise/faults in data measurement setting (e.g. loose apparatus, power line interference, body movements, etc.) or due to some physiological abnormality Anomaly in the cardiac activity of a patient may be any deviation from the normal cardiac activity, for example, ventricular fibrillation, ventricular flutter, ventricular tachycardia and asystole. Anomalous electrical signals of a heart muscle are reflected by deviations in specific portions of the curve from the predicted norm. Anomaly detection in the biomedical signals therefore has increasingly become an important task among researchers and practitioners. For example, it may be used to detect any time periods of unusual ECG beats. The accuracy of the anomaly detection method directly reflects the result of the cardiac disease detection and diagnosis.

The traditional systems and methods provide for some anomaly detection in the cardiovascular signal but do not consider the discrete nature and strict rising and falling patterns of the cardiovascular signal and frequency in terms of hierarchical maxima points and minima points. Hence, there is a need for a technology that provides for detection of window for feature derivations in a dynamic and unsupervised manner, derivation of features mainly dependent on the morphology and strictly rising and falling edge of the signal, exploitation of the nature of rise and fall of the signals in terms of hierarchical maxima points and minima points and their frequency, discovering the repetitions of the combination of features which, in other words, are the patterns in the signal, quantification of information to judge the significance of the repetition or regularity of the patterns and relate the stages of repetition with feature hierarchy that may lead to the dimensionality of the pattern occurrence matrix.

In others words, the technology must provide for discovering the regular and irregular patterns of quasi periodic cardiovascular signal like photoplethysogram (PPG) and electrocardiogram (ECG) which are synchronized with heartbeats and thereby identifying anomalous and non-anomalous phenomena in the cardiovascular signal, where anomalous phenomena encompasses noise or uncertain events as well as abnormal events.

Referring now to the drawings, and more particularly to FIG. 1 through FIG. 13, where similar reference characters denote corresponding features consistently throughout the figures, there are shown preferred embodiments and these embodiments are described in the context of the following exemplary system and/or method.

FIG. 1 illustrates an exemplary block diagram of a system 100 for detecting the anomaly in the cardiovascular signal using hierarchical extremas and repetitions. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
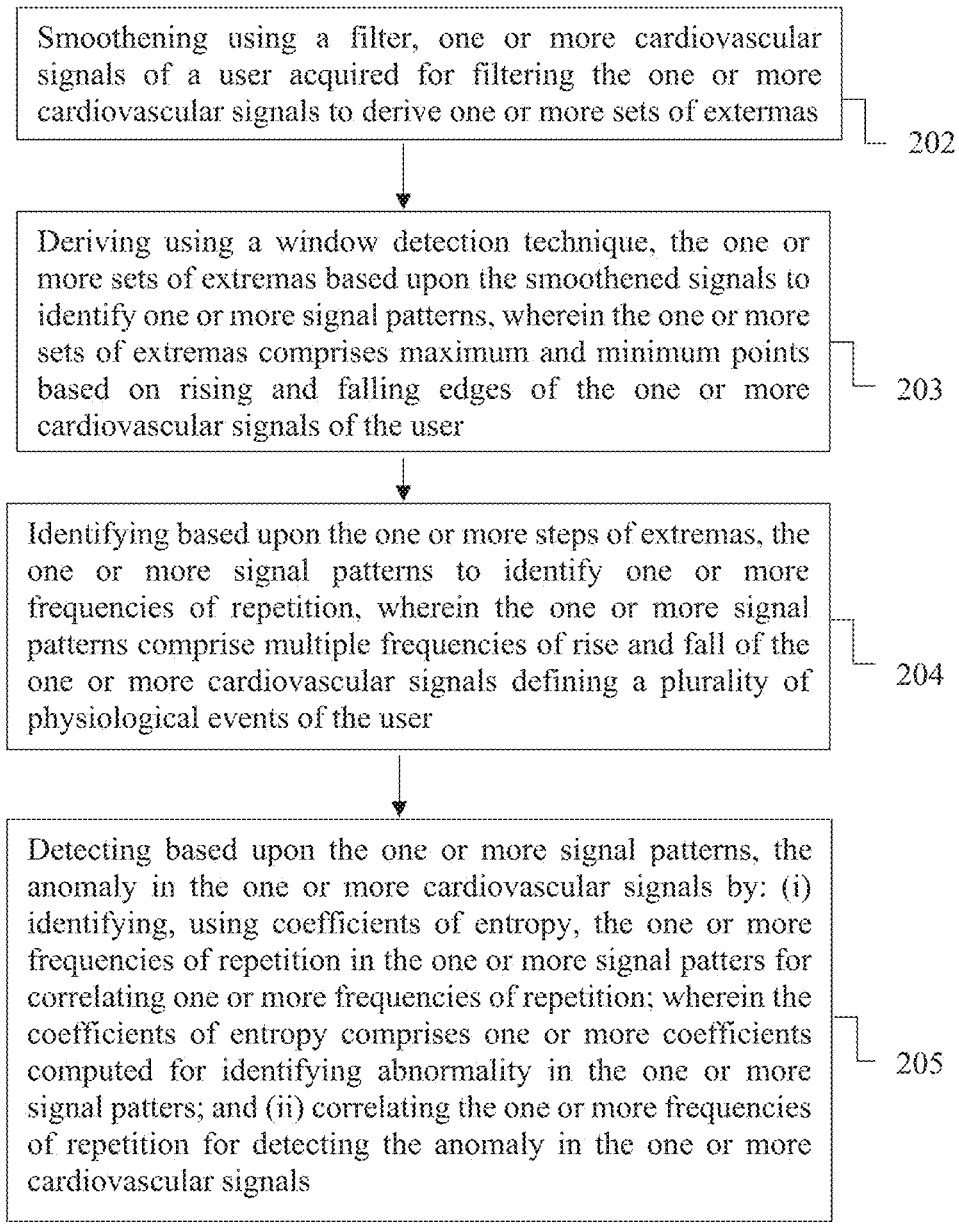
FIG. 2 is a flowchart illustrating the steps involved for detecting the anomaly in the cardiovascular signal using hierarchical extremas and repetitions according to an embodiment of the present disclosure.

FIG. 2, with reference to FIG. 1, illustrates an exemplary flow diagram of a method for detecting the anomaly in the cardiovascular signal using hierarchical extremas and repetitions. In an embodiment the system 100 comprises one or more data storage devices of the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1 and the flow diagram. In the embodiments of the present disclosure, the hardware processors 104 when configured the instructions performs one or more methodologies described herein.

According to an embodiment of the present disclosure, at step 201, the cardiovascular signal acquired may be smoothened for filtering the cardiovascular signal. According to an embodiment, the cardiovascular signal of the user may be acquired by the system 100 using one or more sensors or devices (not shown in the figure). The cardiovascular signal that may be acquired may comprise of a photoplethysmogram (PPG) signal or an Electrocardiogram (ECG) signal or any other cardiovascular signal of a user. The embodiments of the present disclosure may support one or more similar cardiovascular signals (like PPG or ECG) for detecting the anomaly but does not support combination of different types of cardiovascular signal/s. The system 100 may comprise of the one or more sensors, which are capable of acquiring (i.e., sensing, detecting, or gathering) cardiovascular sound signals from the user when placed on or near the user. Examples of the one or more sensors that are suitable for the system 100 may comprise of (but not limited to) an electrocardiogram sensor, acoustic sensor or any other heart monitoring sensor/s (for example, heart-rate monitoring sensor). Similarly, system 100 may also comprise of one or more devices for acquiring heart rate signals or features of the user, for example, a heart rate monitor or an activity monitor.

Figure 3:
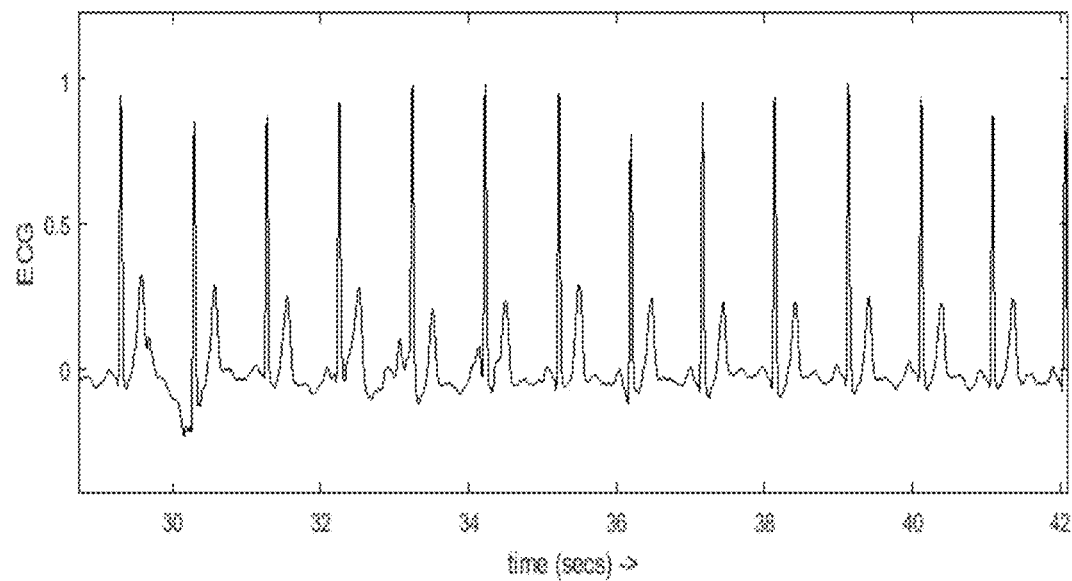
FIG. 3 shows the graphical representation of acquired cardiovascular signals of a user for detecting the anomaly in the cardiovascular signal using hierarchical extremas and repetitions according to an embodiment of the present disclosure.

According to an embodiment of the present disclosure, referring to FIG. 3, the cardiovascular signal of the user acquired by the system 100 may be referred. The embodiment of the present disclosure further support acquiring cardiovascular signal of the user via smartphone platforms such as iOS and Android comprising of a plurality of health or medical applications that acquire and analyze a variety of vital signs (including heart rate signals or other features) through embedded sensors, interconnected devices or peripherals utilizing on occasion analytics and social media. The cardiovascular signal acquired by the sensor may comprise of heart rate signals, sound signals emanating from the heart, blood vessels (i.e., arteries, veins, capillaries, etc.) and/or other portions of the cardiovascular system of the user. The one or more sensors may be placed on the user's precordium or any other locations (for example, on the back) to acquire the cardiovascular signal of the user.

According to an embodiment of the present disclosure, the process of smoothening the cardiovascular signal acquired may now be considered in detail. The cardiovascular signal may encounter various types of artifacts during acquisition, transmission and storage. For example, noises introduced due to power line interference (PLI), body movements, electrode contacts, electromagnetic field interference, respiration movements etc. Presence of inequalities or noises in the cardiovascular signal degrades the signal quality and thus affects the visual diagnosis and feature extraction. In an embodiment, the cardiovascular signal may be smoothened using one or more filters for example, a median filter or a low-pass filter for removing noise or using filtering techniques (or any combinations thereof) for example, Moving Average Low-pass filtering technique. In an embodiment, the low-pass filter is implemented to remove any artifacts or perturbations from the cardiovascular signal acquired. The moving average parameter depends upon the sampling frequency of the cardiovascular signal. In an embodiment, the moving average parameter is selected using $MA_{parameter}=Fs/MA$. Further according to an embodiment, the value of ma is to be selected that the moving average parameter should be less than the percentage quartile of frequency of the cardiovascular signal. In an embodiment, ma has been selected as 25 for obtaining the moving average parameters.

Figure 4:
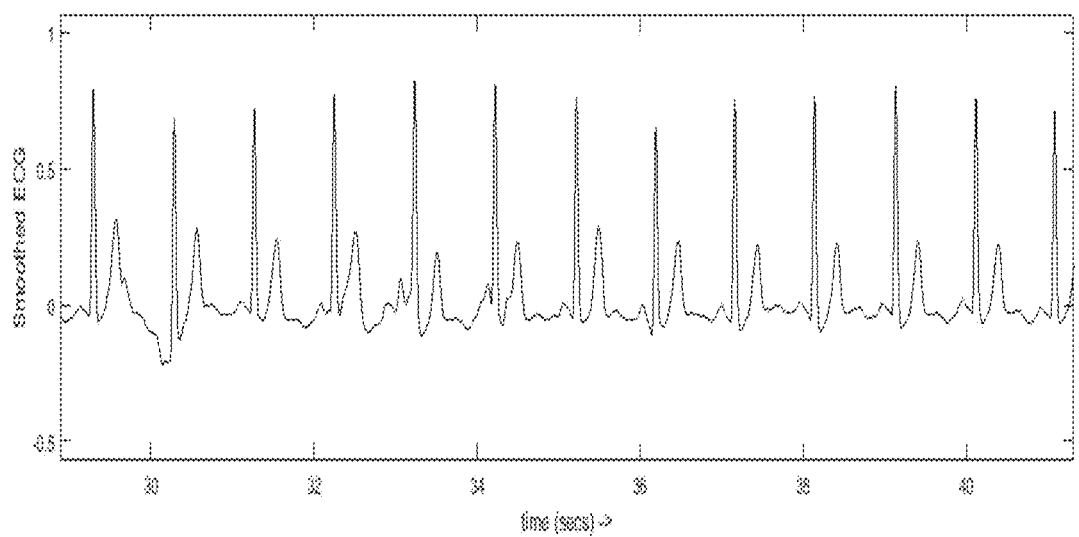
FIG. 4 shows the graphical representation of smoothened cardiovascular signals detecting the anomaly in the cardiovascular signal using hierarchical extremas and repetitions according to an embodiment of the present disclosure.

According to embodiment of the present disclosure, referring to FIG. 4, the cardiovascular signal smoothened using the filter (and by selecting ma as 25) may be referred. The filter (or the low-pass filter) may be implemented in the system 100 using the one or more hardware processors 104 or through a set of micro-processors (not shown in the figure) or any combinations thereof. The filter may also incorporate any suitable filter design technique to remove inequalities or noise. For example, the filter may use well-known filter design techniques from signal processing such as order-matching and transfer-function analysis techniques for removing inequalities or noise.

Figure 5:
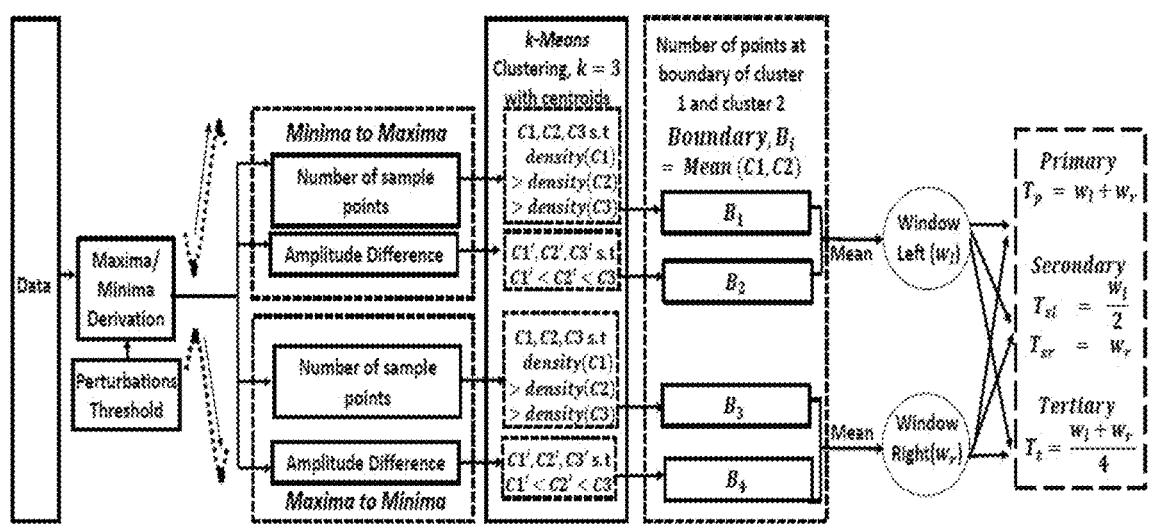
FIG. 5 illustrates a block diagram of a window detection technique for deriving one or more sets of hierarchical extremas for detecting the anomaly in the cardiovascular signal according to an embodiment of the present disclosure.

According to an embodiment of the present disclosure, at step 202, based upon the smoothened cardiovascular signal, one or more sets of hierarchical extremas may be derived using a window detection technique, wherein the one or more sets of hierarchical extremas comprises maximum points and minimum points (also alternatively referred to as maxima points or minima points) based on rising and falling edges maintaining a hierarchy of the cardiovascular signal. The traditional systems and methods do not provide for derivation of hierarchical extremas based strictly upon the rising and falling edges of the cardiovascular signal. The embodiments of the present disclosure provide for derivation of the one or more sets of hierarchical extremas into different hierarchies using the window detection technique by considering n number of stages of rise and fall of the cardiovascular signal. For detecting the anomaly, the three stages may be considered for all computation purposes (an exemplary case may be shown with three stages) and may be termed as primary, secondary and tertiary. Referring to FIG. 5, the architecture or block diagram depicting flow of the window detection technique may be referred.

The process of deriving the one or more sets of hierarchical extremas using the window detection technique may now be considered in detail. According to an embodiment, the window w needs to be computed such that xt<xt+ 1< . . . <xt+w−1 and the same value of w may hold for multiple local maxima points, where xt denotes a local maxima point. According to an embodiment it is further assumed that the amplitude difference between the local maxima point xt and immediately following local maxima point may be have a significant regular difference. Further, it may be assumed that in general strictly increasing edges of the cardiovascular signal may not always happen. There may be a need to provide some relaxation in this regard. This relaxation may not occur frequently in the cardiovascular signal (if it occurs frequently then it becomes repetitive part of the cardiovascular signal and may be patterns of signals to be identified). In an embodiment, for implementing the above conditions, the number of consecutively occurring previous points which are strictly rising and culminating at the local maxima point may be obtained for every local maxima point.

The corresponding amplitude difference of that maxima point and the previous minima point may then be computed and clustering on both the number of previously occurring point as well as on the amplitude differences may then be performed. The value of $w_l$ as a function of the centroids of the clusters corresponding to the number of points and the amplitude differences may then be obtained. According to an embodiment, similar steps may then be performed for local minima points to obtain value of $w_r$. The number of sampling points for primary window, denoted by $T_p$ may be computed as $w_l+w_r$ for detecting the one or more sets of hierarchical extremas (i.e. maxima and minima) hierarchically. In an embodiment, after detection of window length $T_p(T_p=w_l+w_r)$, the one or more sets of hierarchical extremas, i.e. three types of local maximas and minimas, that is primary, secondary and tertiary as basic features may be obtained considering three stages of repetition.

Figure 6:
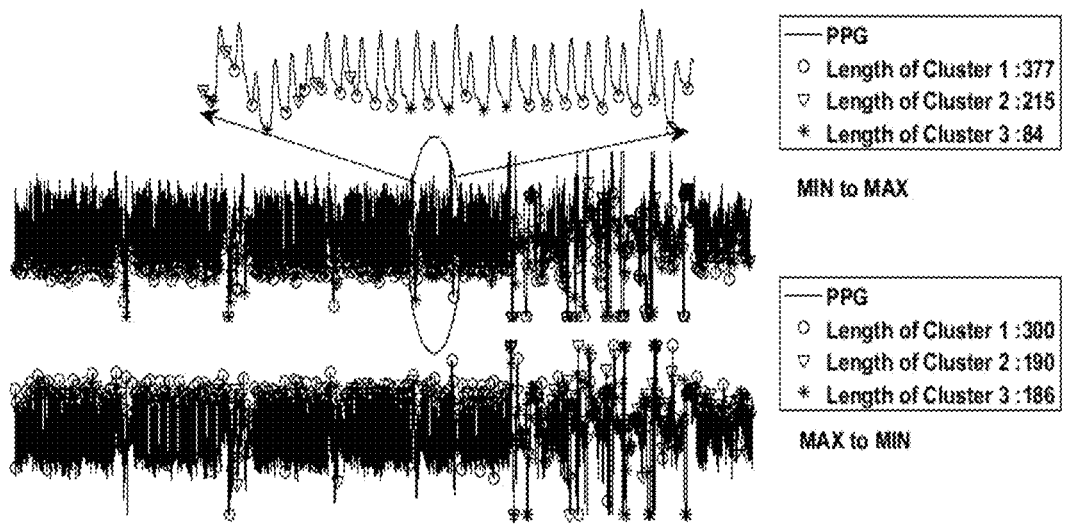
FIG. 6 shows the graphical representation of the number of sampling points derived and the amplitude difference from minima to maxima and from maxima to minima using k-means clustering according to an embodiment of the present disclosure.
Figure 7:
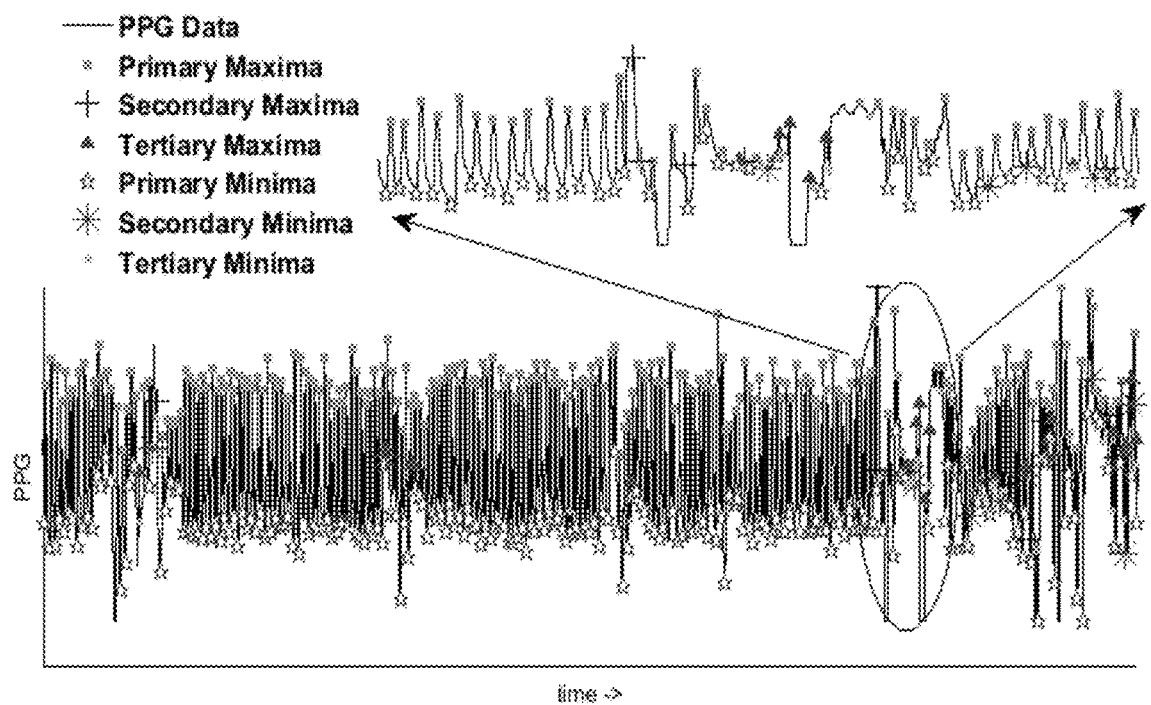
FIG. 7 shows the graphical representation of the one or more extremas derived according to an embodiment of the present disclosure.

According to an embodiment of the present disclosure, referring to FIG. 6, the number of sampling points derived and the amplitude difference from minima to maxima and from maxima to minima using k-means clustering having the number of clusters as 3 may be referred. For minima to maxima, let the centroids be $nc_1$, $nc_2$ and $nc_3$ based on the number of sampling points such that $nc_1>nc_2>nc_3$. (It may be noted that a centroid is considered as a center value for all observations such that the sum of the distance from all the points is minimum. For example, for the point x_1, x_2, x_3 . . . x_n, the centroid will be C=1/N*(x_1+x_2+x_3+ . . . +x_N).

In an embodiment, let the centroids be $c_1$, $c_2$ and $c_3$ based on the amplitude difference such that $c_1<c_2<c_3$ From maxima to minima, let the centroids be $nc_1'$, $nc_2'$ and $nc_3'$ based on the number of sampling points such that $nc_1'>nc_2'>nc_3'$ Let the centroids be $c_1'$, $c_2'$ and $c_3'$ based on the number of sampling points such that $c_1'<c_2'<c_3'$ For minima to maxima, find the boundary of cluster $nc_1$ and $nc_2 \approx B_1$ and find the boundary of cluster $c_1$ and $c_2 \approx B_2$ For maxima to minima, find the boundary of cluster $nc_1'$ and $nc_2' \approx B_3$ and find the boundary of cluster $c_1'$ and $c_2' \approx B_4$ Now, window left may be obtained and denoted as Window Left=$(w_{left})$=mean($B_1$, $B_2$) and window right may be obtained and denoted as Window Right= $(w_{right})$=mean($B_3$,$B_4$) and finally;

Primary window may be obtained and denoted as $T_p = W_{left} + W_{right}$

Secondary window may be obtained and denoted as Left: $T_{sl} = W_{left}/2$

Tertiary window may be obtained and denoted as $T_t = (W_{left}+W_{right})/4$

According to an embodiment of the present disclosure, the one or more sets of hierarchical extremas (comprising of maximum points and minimum points) may be derived based upon the windows detection. In an embodiment, primary maxima may be defined as a local maxima point where on the left side of the maxima, the number of points considered may be at least $w_l$, and the number of points on the right side may be at least $w_r$. For a secondary local maxima, the number of points considered at left side ($T_{sl}$) may be at least $w_l/2$ and the number of points considered at right side ($T_{sr}$) may be at least $w_r$. Similarly, for the tertiary local maxima, the number of points considered for both left and right sides are $w_l+w_r/4$. Referring to FIG. 5, the functional block diagram depicting window detection for deriving the one or more sets of hierarchical extremas may be referred. Similar approach may be followed for deriving minimas or minimum points. In an embodiment, the maxima or the maximum points may be derived using below algorithm.

INPUT:
  $MAX_1,......J - 1$: $I^{st}, 2^{nd},.........(J - 1)$th level maximas
  $win_{jl}, win_{jr}$: Window size on the left, right
  $T_3$: Distance between two maximas
  $D_{MA}$: Smoothened signal $x_k$ with k = 1, 2, 3, ... ... .N, N = length (D)using $MA_1$ and $MA_2$
OUTPUT:
  $MAX_j$: $J^{th}$ level maxima indices
BEGIN
  M = Find Indices of $\hat{D}$ s.t $\hat{x}k - win_{jl} < t \hat{x}k - win_{jl} + 1$ ... ... ..., $< \hat{x}k - 1 < \hat{X}k > \hat{x}k + 1 > ... > \hat{x}k + win_{jr}$
  $M_J$ = Discard Indices $M_k$ in M s.t | $M_k - M_{k-1}$ | < $T_3$ $$MAX_J = M_J - \bigcup_{t=0}^{J-1} MAXt$$

END

For primary, J=1, $win_{l1}=win_l$; $win_{r1}=win_r$; $T_3=T_P$; $T_P=w_l+w_r$
For secondary, J=2, $win_{l2}=T_{sl}$; $win_{r2}=T_{sr}$; $T_3=0$
For tertiary, J=3, $win_{l3}=T_t$; $win_{l3}=T_t$; $T_3=0$ Referring to FIG. 7, using the above algorithm and the window detection technique explained above, the one or more extremas comprising of the maximum points and minimum points (that is primary, secondary and tertiary maximas and minimas) based on rising and falling edges of the cardiovascular signal of the user may be referred.

According to an embodiment of the present disclosure, at step 203, based upon the one or more sets of hierarchical extremas, one or more elements of signal patterns may be identified, wherein the one or more elements of signal patterns comprise multiple frequencies and significance associated with the cardiovascular signal for defining a plurality of physiological events of the user or noise. According to an embodiment, the patterns in the cardiovascular signal correspond to repetition, and pattern discovery corresponds to combine the repetitions in the cardiovascular signal. In an embodiment, the meaning of the word repetition may change from one cardiovascular signal to another signal. In an embodiment, patterns are represented as functions and combinations of the basic features and derived features and the significance of the one or more elements of signal patterns comprises obtaining a lower triangular matrix based upon a hierarchy of extremas, wherein the lower triangular matrix comprises number of occurrences of the one or more elements of signal patterns to identify variability in the cardiovascular signal.

Figure 8A:
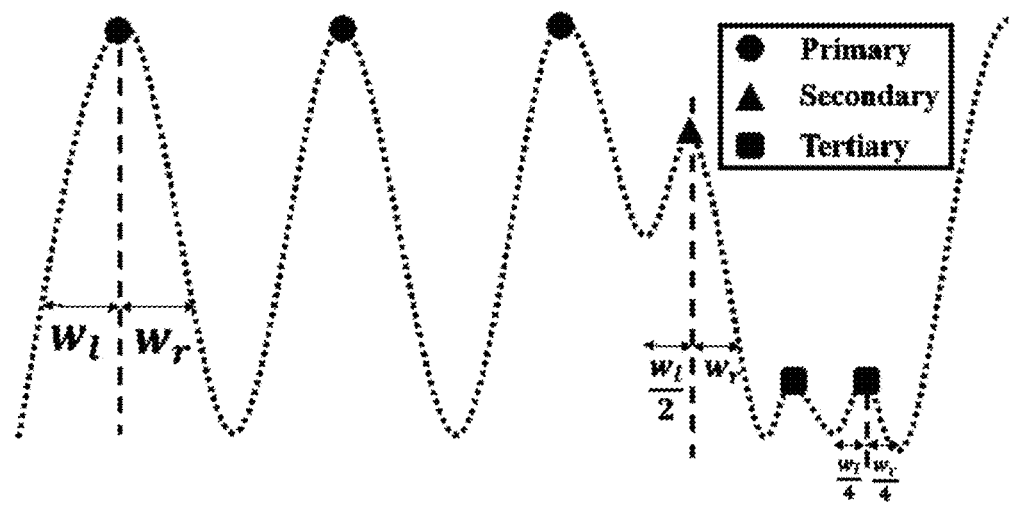
FIG. 8(a) shows the graphical representation of the number of frequencies or occurrences of the primary, secondary and tertiary maxima's according to an embodiment of the present disclosure.
Figure 8B:
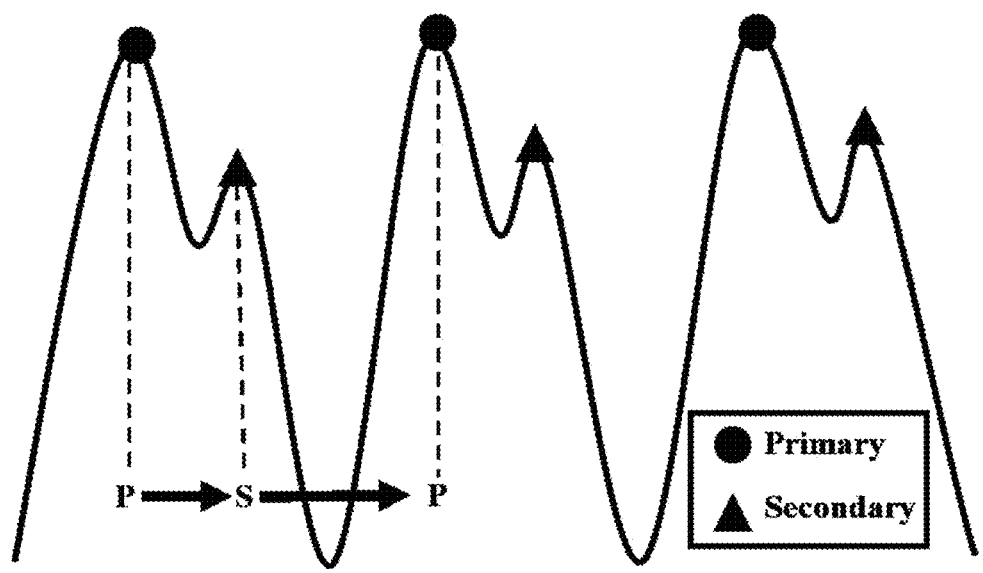
FIG. 8(b) shows the graphical representation of one or more elements of signal patterns combining two levels of features according to an embodiment of the present disclosure.

According to an embodiment, the steps of identifying the one or more elements of signal patterns may now be considered in detail. Referring to FIG. 8(*a*), the number of frequencies or occurrences of the primary, secondary and tertiary maximas may be observed. According to an embodiment, if in a part of the cardiovascular signal, primary maxima is followed by primary maxima, then this segment of the cardiovascular signal may be denoted by 'PP' and may be described as dual patterns. Referring to FIG. 8(*b*) we can observe a plurality of patterns as 'PS', 'PT' and consequently as 'SP', 'SS', 'ST', 'TP', 'TS', 'TT'. Similarly, the frequencies or repetitions, that is, the number of occurrences or frequencies of primary minima, secondary minima and tertiary minima (and corresponding to the minimas) may be obtained (not shown in the figure).

According to an embodiment of the present disclosure, for maxima of the signal, a 3×3 square matrix $MAT_1$ may be generated where each matrix element denotes the occurrences or frequencies or repetitions in the dual patterns in the whole signal. For example, $MAT_1(1,1)$ corresponds to frequency of primary maxima followed by primary maxima. Similarly, a 3×3 square matrix $MAT_2$ may be generated using local minima points. Further, the dual patterns may also be represented in the number of sampling points, that is, another 3×3 square matrix $MAT_3$ may be generated where each matrix element may correspond to the total number of sampling points corresponding to the particular dual pattern. For example, $MAT_3(1,1)$ corresponds to the total number of sampling points between all the instances of primary maxima followed by primary maxima. Similarly, according to an embodiment, a 3×3 square matrix $MAT_4$ may be generated by using local minima point where each matrix element corresponds to the total number of sampling points between all the instances of primary minima followed by primary minima. Referring to tables 1, 2, 3 and 4 below, examples values of $MAT_1$, $MAT_2$, $MAT_3$ and $MAT_4$ for PPG signals from one or more users may be referred, where table 1 shows example values of $MAT_1$, table 2 shows example values of $MAT_2$, table 3 shows example values of $MAT_3$ and table 4 shows example values of $MAT_4$. The embodiment of the present disclosure considers three levels of the local maximas and/or minimas, that is, primary, secondary and tertiary. For identifying the frequencies or repetitions, two levels of combinations, that is, 'PP', 'PS' . . . 'TT' were considered. The embodiments of the present disclosure support generalizing this to three levels of combining features resulting in four 3-dimensional patterns, that is, 'PPP', 'PPS' . . . 'TTT'. Further, according to an embodiment, this may be generalized to any number of levels.

TABLE 1

$MAT_1$

| | Primary Maxima | Secondary Maxima | Tertiary Maxima |
|---|---|---|---|
| Primary Maxima | 312 | 17 | 27 |
| Secondary Maxima | 14 | 3 | 5 |
| Tertiary Maxima | 30 | 2 | 10 |

TABLE 2

$MAT_2$

| | Primary Maxima | Secondary Maxima | Tertiary Maxima |
|---|---|---|---|
| Primary Maxima | 343 | 18 | 23 |
| Secondary Maxima | 15 | 1 | 12 |
| Tertiary Maxima | 27 | 8 | 11 |

TABLE 3

$MAT_3$

| | Primary Maxima | Secondary Maxima | Tertiary Maxima |
|---|---|---|---|
| Primary Maxima | 31137 | 1159 | 1358 |
| Secondary Maxima | 818 | 112 | 166 |
| Tertiary Maxima | 2236 | 80 | 433 |

TABLE 4

$MAT_4$

| | Primary Maxima | Secondary Maxima | Tertiary Maxima |
|---|---|---|---|
| Primary Maxima | 29723 | 1514 | 1299 |
| Secondary Maxima | 870 | 89 | 1034 |
| Tertiary Maxima | 1678 | 518 | 641 |

According to an embodiment of the present disclosure, at step 204, the anomaly in the cardiovascular signal may be detected by determining, occurrences and randomness of occurrences of the one or more elements of signal patterns by computing an entropy of occurrences of the one or more elements of signal patterns and further by identifying, significance of the occurrences repetitions or of the one or more elements of signal patterns, based upon the occurrences and randomness of occurrences. Referring to FIG. 9, the frequencies or repetitions based upon the one or more sets of hierarchical extremas, that is, the number of occurrences or frequency of primary maxima (P), secondary maxima (S) and tertiary maxima (T) may be referred.

According to an embodiment of the present disclosure, the steps for identification of the occurrences and randomness of occurrences in the one or more elements of signal patterns (or deriving the mode of the frequency of the dual patterns of the combination of features, that is, ('PP', 'PS' . . . 'TT') and the significance may now be considered in detail. In an embodiment, the significance of repetitions of the one or more elements of signal patterns comprises obtaining a lower triangular matrix based upon a hierarchy of extremas, wherein the lower triangular matrix comprises number of occurrences of the one or more elements of signal patterns to identify variability in the cardiovascular signal. In an embodiment, the uni-modality may indicate the distribution of the occurrences as singular dominance whereas the multi-modality may indicate multiple dominant dual patterns depicting a lack of stability in the side of the cardiovascular signal. Referring to FIG. 9 again, a lower triangular matrix $(MAT3)_L$ using $MAT_3$ may be generated for further joining the patterns like 'PP', 'SP' to get a broader view of the frequencies or repetitions of the one or more elements of signal patterns. According to an embodiment, the coefficients of entropy (also herein referred to as Shannon's entropy) may be defined for a random variable X with sample space $S_x=x_i$: $i=1, 2, 3, \ldots$ n: $H(X)=-\Sigma_i pi(X)\log 2pi(X)$. Further, the Shannon's entropy for $(MAT3)_L$ may be defined as $F_{ent}$ to identify the significance of repetitions of the one or more elements of signal patterns.

According to an embodiment of the present disclosure, the one or more threshold values (comprising of a upper and a lower value of $F_{ent}$) may be defined. The one or more threshold values or the upper and the lower values may be defined as:

Upper threshold ($F_{up}$): If the occurrences of all the six patterns, that is, ('PP', 'PS' . . . 'TT' are equally probable $(MAT3)_L$, that is, the signal shows a randomness indicating multi-modal pattern occurrences resulting in multiple dominant patterns (indicating lower chances of repetitions).

$$\sum_{pattern=1}^{6} Ppattern = 1; \therefore P_{pattern} \Rightarrow \frac{1}{6} = 0.167$$

Hence, the probability of each of the pattern (from amongst the one or more elements of signal patterns) is 0.167. The $F_{ent}$ using $P_{pattern}$ may be obtained as:

$F_{ent}=\Sigma_{pattern=1}^{6} P\text{pattern}*\log 2P_{pattern}$ $(F_{up})=\Sigma_{pattern=1}^{6} 10.167*\log 2\ 0.167 \Rightarrow 2.5850$ Hence, the upper threshold of $F_{ent} \rightarrow F_{up}$ is 2.5850.

Lower threshold ($F_{low}$): In an embodiment, if amongst the six patterns any one of them is dominant and the other patterns do not repeat at all, the probability of the one pattern will be one and for other patterns will be 0. The coefficients of entropy in this case may be obtained as $F_{low}=1.0*\log 2\ 1.0 \Rightarrow 0$. However 0 is a crude lower bound for the entropy. Multiple PPG datasets where the signals correspond to healthy users and not possessing any noise and having entropy values close to 1.5 have been observed.

Figure 11:
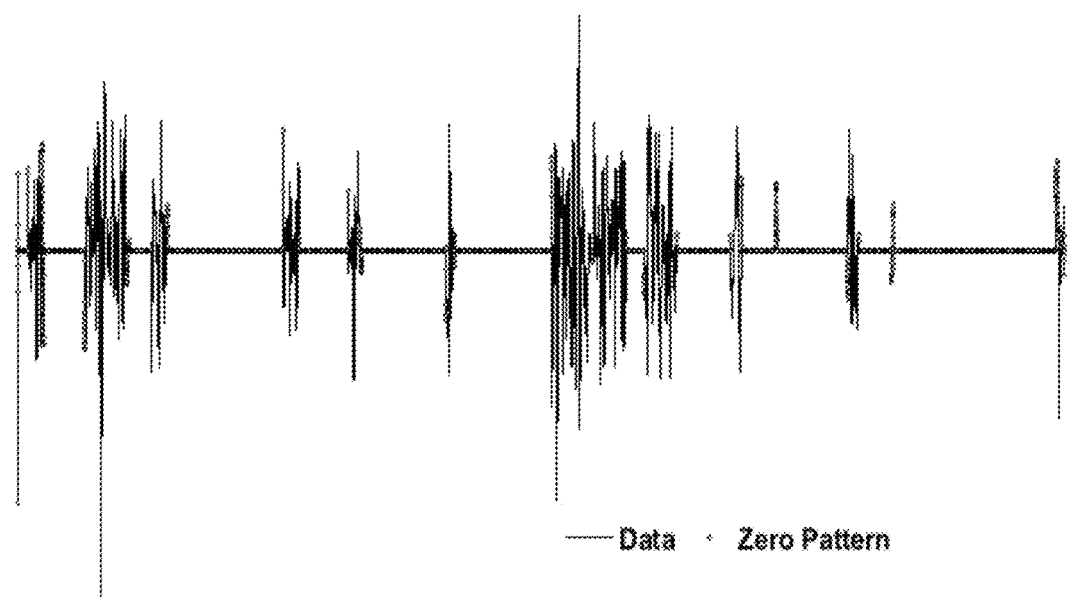
FIG. 11 shows the graphical representation of one or more zero patterns identified in the cardiovascular signal according to an embodiment of the present disclosure.

According to an embodiment of the present disclosure, based upon the one or more threshold values and the one or more elements of signal patterns, one or more zero patterns may be obtained. The amplitude difference of the consisting sampling points of each of the patterns segments such as 'PP', 'PS' may be evaluated. In any such segment, if 70% of the sampling points show no amplitude difference, that segment may be marked as a zero-pattern and may be denoted as $Z_p$. Thus, the consecutive sampling points that show no amplitude difference are marked as zero pattern. According to an embodiment, the cardiovascular signal may be divided into different segments. For example, considering x is the proportion of the one or more zero patterns and 1−x be the proportion of non-zero patterns. In x segments if 70% of the sampling points show no amplitude difference then it is considered as the zero pattern. The one or more zero patterns are the prominent patterns which may occur due to machine faults, removal of device lead or due to disconnection between device and the logger system of the patient. Referring to FIG. 11, the one or more zero patterns identified may be referred.

According to an embodiment of the present disclosure, the frequencies or repetitions may be correlated for detecting the anomaly in the cardiovascular signal. This comprises removing of the one or more zero patterns and determining one or more quantitative values, also known as a significance score for classifying the one or more elements of signal patterns as anomalous and non-anomalous. The cardiovascular signal may comprise of anomalous phenomena showing multiple dominance of the one or more elements of signal patterns, however there may be certain patterns from amongst the one or more elements of signal patterns which are significant. To identify the significant patterns, the one or more zero patterns may be removed and the frequencies or repetitions identified using the coefficients of entropy may be re-evaluated. This may now be considered in detail. For example, considering x is the proportion of the one or more zero patterns and 1−x be the proportion of non-zero patterns. The significance score denoted by F may then be proposed. F may be computed as:

$$F_s = x + (1-x)\frac{F_{ent}}{F_{up}}$$

After removing the one or more zero patterns, if the signal has many significant maxima points, it may become anomalous. Suppose the number of significant patterns are 4. Let the threshold for detecting the anomalous phenomena be 2 obtained as below:

$$F_{\frac{ent}{partial}} = -4 \times \frac{1}{4\log2\left(\frac{1}{4}\right)} = 2$$

Hence, the significant score $F_s$ considering the one-third zero pattern, that is, x=33% may be obtained as:

$$F_s = 0.33 + \frac{(1-0.33)2}{2.58} \approx 0.84$$

The F may then be relaxed $F_{s/anomalous}=0.80$ may be taken as the threshold to classify a signal as anomalous or non-anomalous.

According to an embodiment of the present disclosure, finally, if the coefficients of entropy (that is, entropy of time-series) is greater than $F_{s/anomalous}$, the cardiovascular signal may be considered as anomalous. That is:

If coefficients of entropy > $F_{s/anomalous}$
Signal is anomalous
else
Signal is Non - anomalous
    end According to an embodiment of the present disclosure, an experimental analysis, data sets and data descriptions on the data sets used in proposed methodology may now be considered in detail. In an embodiment, referring to table 5 below, six different real life bio medical data sets used.

TABLE 5

| Data Sets | Data Category | Number of Signals | Sampling Frequency | Duration |
|---|---|---|---|---|
| $PPG_{LabC}$ | I | 16 | 60 | 5 minutes |
| $PPG_{LabN}$ | II | 9 | 60 | 5 minutes |
| $PPG_{Physionet}$ | III and IV | 181 | 125 | 5 minutes |
| $PPG_{Capnobase}$ | III | 42 | 300 | 8 minutes |
| $PPG_{CAP}$ | II and IV | 77 | 256 | >>60 minutes |
| $PPG_{Physionet}$ | III and IV | 98 | 125 | >>6 minutes |

According to an embodiment of the present disclosure, the different data sets may be now be considered in detail (with respect to the data they contain and the method of obtaining the data).

Figures 12A, 12B:
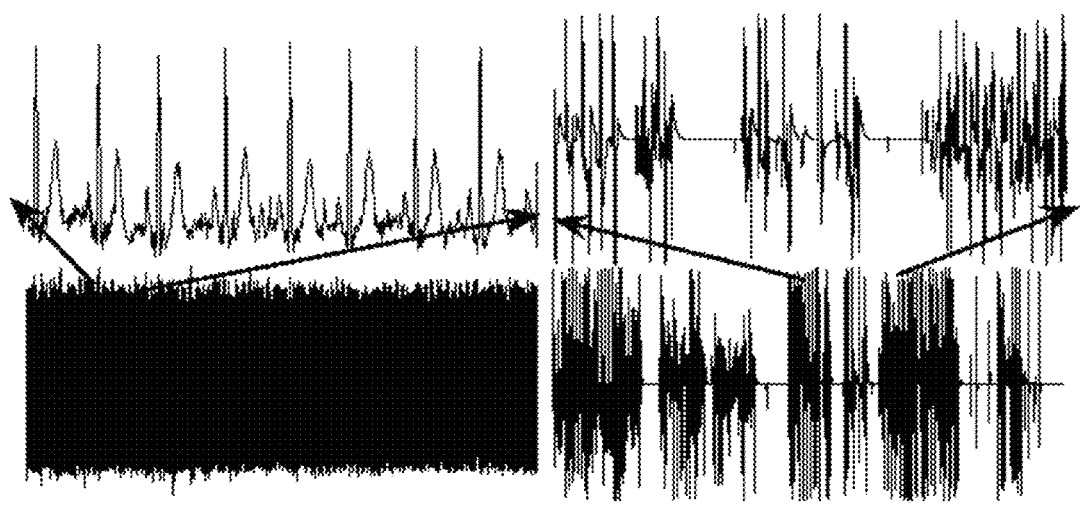
FIG. 12(a) shows the graphical representation of clean Electrocardiography (ECG) data sets according to an embodiment of the present disclosure.
FIG. 12(b) shows the graphical representation of noisy ECG data sets according to an embodiment of the present disclosure.
Figure 13:
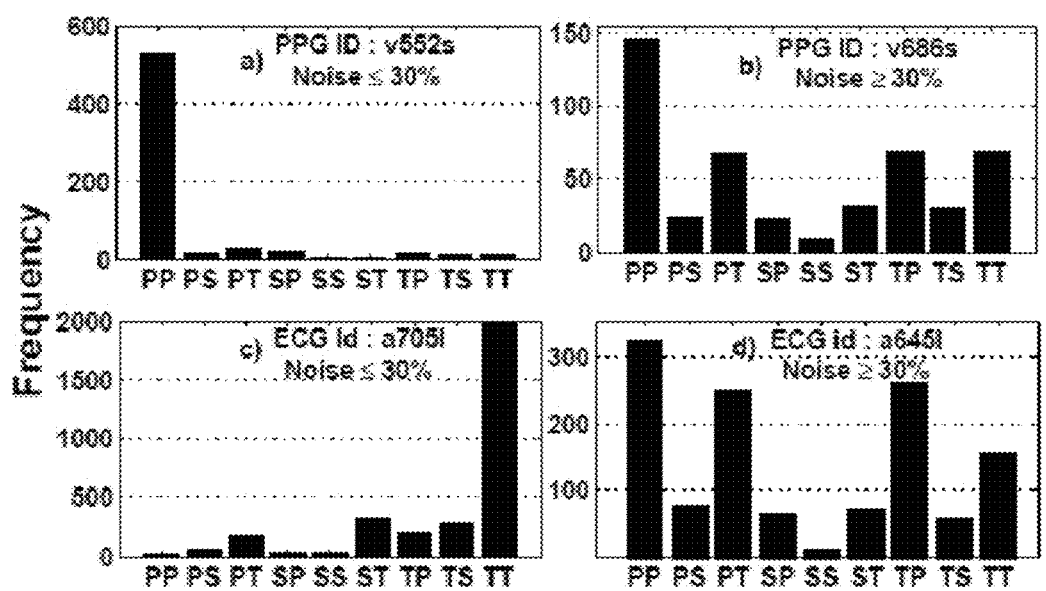
FIG. 13 shows the graphical representation of a uni-modal versus a multi-modal distribution of the one or more elements of signal patterns with respect to varying noise percentages in the corresponding (a) clean, (b) noisy Photoplethysmogram (PPG) signals and (c) clean, (d) noisy ECG signals according to an embodiment of the present disclosure.

- Data set $PPG_{LabC}$ comprises fingertip PGG data obtained from 16 persons (11 males and 5 females) having ages between 20 to 50 years. The data was obtained for 5 minutes duration, where each user kept the finger at same place without any movements ensuring signals without noise.
- Data set $PPG_{LabN}$ comprises 16 PPG data with 5 minutes duration where each user moved the finger multiple time for incorporating motion artifacts in the signal. Noise duration is ≥30% of the total duration.
- Data set $PPG_{Physionet}$ comprises 181 data sets having 5 minutes duration obtained randomly from Physionet Challenge database. The data sets comprised of motion artifacts which were annotated and re-evaluated.
- Data set $PPG_{Capnobase}$ comprises 184 data sets having 8 minutes duration obtained from Capnobase database. The data sets comprises of motion artifacts but with very less corrupted percentage, that is, >5%. Further, 19 motion artifacts contaminated data sets from 42 data sets were considered for evaluation.
- Data set $PPG_{CAP}$ comprises 77 PPG signals obtained from Cyclic Alternating Pattern (CAP) database which comprised of signals with respected to higher body movements of the users.
- Data set $PPG_{Physionet}$ comprises 98 ECG signals having 5 to 6 minutes duration obtained from the Physionet Challenge database (as referred to above). The noisy portions were annotated and re-evaluated. Referring to FIGS. 12(a) and 12(b), an example of clean and noisy ECG data sets may be referred to, where FIG. 12(a) shows graphically the clean ECG data sets while FIG. 12(b) shows graphically the noisy ECG data sets.

Figure 10C:
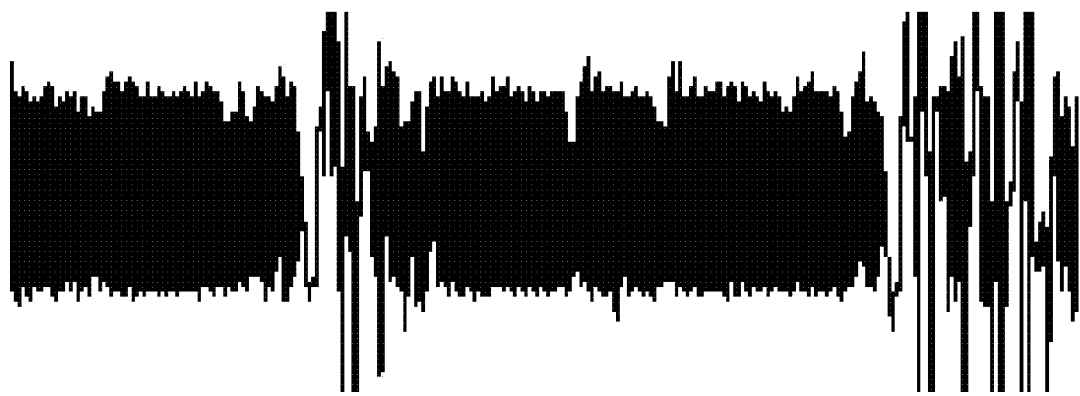
Figure 10D:
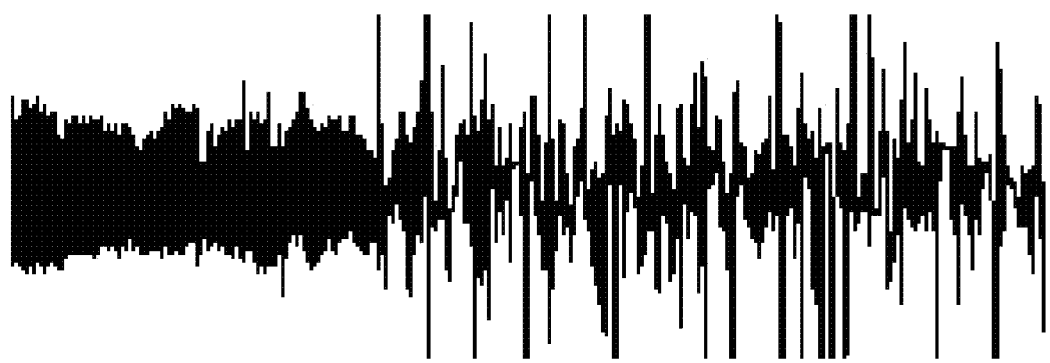
Figure 10E:
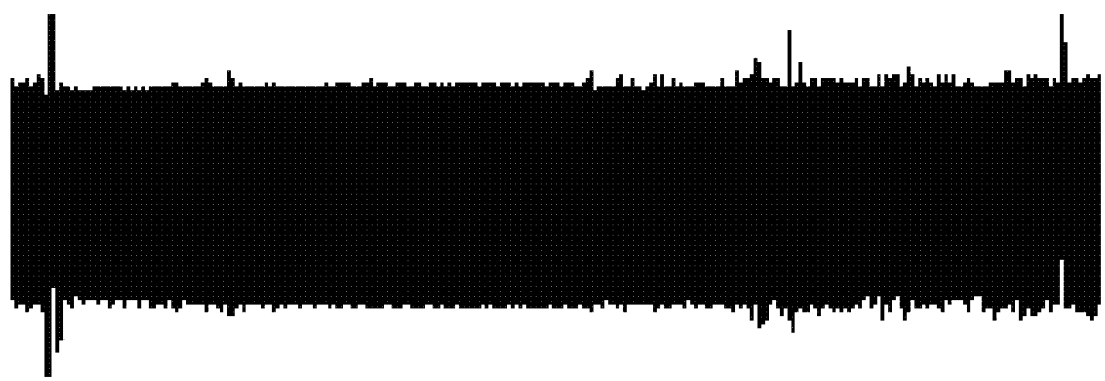
Figure 10F:
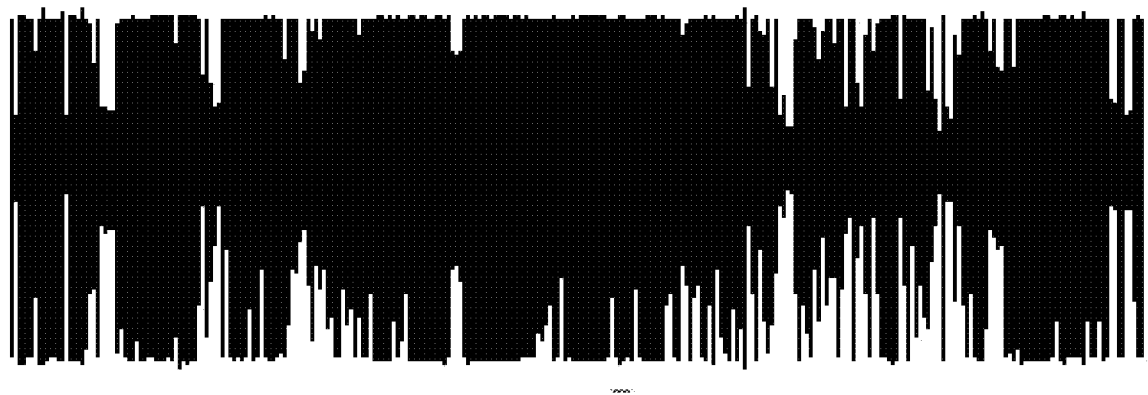

According to an embodiment of the present disclosure, referring to FIG. 10(a) to FIG. 10(f), examples of waveforms taken randomly from the data sets referred to in table 5 and described above may be referred. FIG. 10(a) shows $PPG_{LabC}$ lab data (clean) with entropy=1.5757. FIG. 10(b) shows $PPG_{LabN}$ lab data (noisy) with entropy=2.1168. Further, FIG. 10(c) shows $PPG_{Physionet}$ Physionet challenge 15 data (noise=22%) with entropy=1.3939 and FIG. 10(d) shows $PPG_{Physionet}$ Physionet challenge 15 data (noise=59%) with entropy=2.2125. Finally referring to FIGS. 10(e) and 10(f), $PPG_{Capnobase}$ Capnobase data (noise=0.6756%) with entropy=0.0933 and $PPG_{CAP}$ CAP data (noise=90%) with entropy=2.07 respectively may be referred.

According to an embodiment of the present disclosure, the performance evaluation of the classification of the cardiovascular signal as anomalous and non-anomalous may now be considered with respect to sensitivity, specificity and accuracy measurement on the data sets (of the cardiovascular signal) may now be observed in detail. The present disclosure helps in deriving accurate physiological parameters from the biomedical signals (such as PPG or ECG) as compared to the traditional systems and methods.

TABLE 6

Performance Analysis

| Data sets | Data category | Average Entropy | Sensitivity | Specificity | Accuracy |
|---|---|---|---|---|---|
| $PPG_{LabC}$ | I | Clean: 1.129 | 100 | 0/0 | 100 |
| $PPG_{LabN}$ | II | Noisy: 2.160 | 0/0 | 88 | 88 |
| $PPG_{Physionet}$ | III and IV | Noisy: 2.290 Clean: 1.559 | 81.26 | 77.52 | 79.20 |
| $PPG_{Capnobase}$ | III | Clean: 0.807 | 90 | 0/0 | 90 |
| $PPG_{Cap}$ | IV | Noisy: 2.522 | 0/0 | 96.10 | 96.10 |
| $PPG_{Physionet}$ | III and IV | Noisy: 2.287 Clean: 1.568 | 87.5 | 80 | 83.67 |

According to an embodiment table 6 above, it may be observed that the cardiovascular signal having less percentage of noise show uni-modal pattern while the cardiovascular signal having greater percentage of noise resemble multi-modal pattern. Further, this phenomena may be observed graphically referring to FIG. 13. Referring to FIG. 13 again, a histogram plot showing the uni-modal versus the multi-modal distribution of the one or more elements of signal patterns with respect to varying noise percentages in the corresponding (a) clean, (b) noisy PPG signals and (c) clean, (d) noisy ECG signals may be referred. Further, referring to table 6 again, in case of the data set $PPG_{LabC}$, the present disclosure depicts a sensitivity of 100% and an average entropy score of 1.129 thereby showing no anomalous phenomena as it belongs to category I. Referring to table 6 again, the data set $PPG_{LabN}$ depicts a high specificity of 88% with average entropy of 2.16 thus indicating anomalous phenomenon as it belongs to category II. The data set $PPG_{Physionet}$ contains a wide range of percentages of motion artifacts with physiological abnormalities in PPG signals. According to an embodiment, the proposed methodology achieved an average entropy of 2.29 for noisy signals (having noise ≥30%) and 1.559 for clean signals noise <30%. This resulted in the classification of both anomalous and non-anomalous signals, with an overall sensitivity of 81.26, specificity of 77.52, and accuracy of 79.20 percent as it belongs to category III and IV.

According to an embodiment of the present disclosure, referring to table 6 again, for the data set $PPG_{Capnobase}$, belonging to category II, the proposed methodology provided entropy of 2.22 resulting in sensitivity score as 90 indicating 17 signals having non-anomalous phenomena out of 19. Further, referring to table 6 again, the data set $PPG_{CAP}$ from category IV having entropy 2.22 contains very high percentage of motion artifacts. The proposed methodology detected 74 out of 77 anomalous phenomenon correctly in this case.

According to an embodiment of the present disclosure, referring to table 6 again, for the data set $ECG_{Physionet}$ comprises ECG signals which contain varying percentage of noise along with physiological abnormalities belonging to category III and IV. The proposed methodology achieved an average entropy of 2.2874 for noisy signals (having noise ≥30%) and 1.568 for clean signals noise <30%. Thus, proposed disclosure extract the one or more elements of signal patterns and their significance relatively well, classifies the cardiovascular signal as anomalous and non-anomalous and thus detects the non-anomalous signal with a high degree of accuracy in comparison to the traditional systems and methods.

In an embodiment, the memory 102 can be configured to store any data that is associated with the detection of anomaly in cardiovascular signal using hierarchical extremas and repetitions. In an embodiment, the information pertaining to the cardiovascular signal acquired, smoothened, the one or more sets of hierarchical extremas, the one or more elements of signal patterns, the frequencies of repetition and the coefficients of entropy etc. are stored in the memory 102. Further, all information (inputs, outputs and so on) pertaining to the detection anomaly in the cardiovascular signal using hierarchical extremas and repetitions may also be stored in the database, as history data, for reference purpose.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, BLU-RAYs, flash drives, disks, and any other known physical storage media.

It is intended that the disclosure and examples be considered as exemplary only, with a true scope and spirit of disclosed embodiments being indicated by the following claims.

What is claimed is:

1. A method for detecting an anomaly in a cardiovascular signal using hierarchical extremas and repetitions, the method comprising a processor implemented steps of:
    smoothening, using a filter, the cardiovascular signal acquired for filtering the cardiovascular signal;
    deriving, using a window detection technique, one or more sets of hierarchical extremas, based upon the smoothened cardiovascular signal, wherein the one or more sets of hierarchical extremas comprises maximum points and minimum points based on rising edges and falling edges of the cardiovascular signal, wherein each level of hierarchy in the one or more sets of hierarchical extremas represents a different window size of detection, and wherein the window detection technique to derive the one or more sets of hierarchical extremas comprising the steps of:
        deriving a number of sampling points and amplitude difference from minima to maxima and maxima to minima;
        performing clustering on the number of sampling points and the amplitude difference from the minima to maxima using k-means clustering to derive a number of clusters with centroids;
        performing clustering on the number of sampling points and the amplitude difference from the maxima to minima using the k-means clustering to derive a number of clusters with centroids;
        determining a plurality of boundaries of the number of clusters for the minima to maxima;
        determining a plurality of boundaries of the number of clusters for the maxima to minima;
        obtaining a value of window left ($w_l$) as a function of the plurality of boundaries of the number of clusters corresponding to the number of sampling points and the amplitude difference from the minima to maxima;
        obtaining a value of window right ($w_r$) as a function of the plurality of boundaries of the number of clusters corresponding to the number of sampling points and the amplitude difference from the maxima to minima; and obtaining a primary window ($T_p$), a secondary window ($T_{st}$) and a tertiary window ($T_t$) using the obtained value of $w_l$ and $w_r$, for deriving the one or more sets of hierarchical extremas, wherein the Vis represented as $T_p=w_l+w_r$, the $T_{st}$ is represented as $T_{st}=w_p/2$ and the $T_t$ is represented as $T_t=(w_l+w_r)/4$;

identifying, one or more elements of signal patterns, based upon the one or more sets of hierarchical extremas, wherein the one or more elements of signal patterns comprise multiple frequencies and significance associated with the cardiovascular signal for defining a plurality of physiological events of the user or noise, wherein identifying the significance of the one or more elements of the signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal;

detecting, the anomaly in the cardiovascular signal by:
determining occurrences of the one or more elements of signal patterns;
determining randomness of occurrences of the one or more elements of signal patterns, by computing an entropy of occurrences of the one or more elements of signal patterns, wherein the entropy comprises randomness of the one or more elements of signal patterns computed based upon probabilities of repetitions of the one or more elements of signal patterns, and wherein determining the randomness of occurrences of the one or more elements of signal patterns comprises obtaining one or more threshold values based upon an equi-probable occurrence of the one or more elements of signal patterns for classifying the one or more elements of signal patterns; and
identifying, significance of repetitions of the one or more elements of signal patterns, based upon the occurrences and randomness of occurrences to detect the anomaly in the cardiovascular signal, wherein identifying the significance of repetitions of the one or more elements of signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal.

2. The method of claim 1, wherein the step of identifying the significance of the one or more elements of signal patterns further comprises evaluating entropy of elements of a lower triangular matrix based upon frequencies and number of points in the one or more elements of signal patterns to detect randomness of the one or more elements of signal patterns.

3. The method of claim 1, wherein the step of identifying the one or more elements of signal patterns is preceded by:
(i) detecting, one or more zero patterns in the cardiovascular signal based upon the one or more sets of hierarchical extremas; and
(ii) filtering, the one or more zero patterns, based upon a comparison of the one or more zero patterns and a predefined threshold to detect the anomaly in the cardiovascular signal.

4. The method of claim 1, wherein the step of identifying the one or more elements of signal patterns further comprises identifying uni-modal and multi-modal patterns in the cardiovascular signal based upon the occurrences of the one or more elements of signal patterns to detect the anomaly.

5. The method of claim 1, wherein the step of obtaining the one or more threshold values comprises computing an upper threshold value based upon occurrences and henceforth entropy of the one or more elements of signal patterns to detect the anomaly.

6. A system for detecting an anomaly in a cardiovascular signal using hierarchical extremas and repetitions, the said system comprising:
a memory storing instructions;
one or more communication interfaces; and
one or more hardware processors coupled to the memory via the one or more communication interfaces, wherein the one or more hardware processors are configured by the instructions to:
smoothen, using a filter, the cardiovascular signal acquired for filtering the cardiovascular signal;
derive, using a window detection technique, one or more sets of hierarchical extremas, based upon the smoothened cardiovascular signal, wherein the one or more sets of hierarchical extremas comprises maximum points and minimum points based on rising edges and falling edges of the cardiovascular signal, wherein each level of hierarchy in the one or more sets of hierarchical extremas represents a different window size of detection, and wherein the window detection technique to derive the one or more sets of hierarchical extremas comprising the steps of:
deriving a number of sampling points and amplitude difference from minima to maxima and maxima to minima;
performing clustering on the number of sampling points and the amplitude difference from the minima to maxima using k-means clustering to derive a number of clusters with centroids;
performing clustering on the number of sampling points and the amplitude difference from the maxima to minima using the k-means clustering to derive a number of clusters with centroids;
determining a plurality of boundaries of the number of clusters for the minima to maxima;
determining a plurality of boundaries of the number of clusters for the maxima to minima;
obtaining a value of window left ($w_l$) as a function of the plurality of boundaries of the number of clusters corresponding to the number of sampling points and the amplitude difference from the minima to maxima;
obtaining a value of window right ($w_r$) as a function of the plurality of boundaries of the number of clusters corresponding to the number of sampling points and the amplitude difference from the maxima to minima; and
obtaining a primary window ($T_p$), a secondary window ($T_{st}$) and a tertiary window ($T_t$) using the obtained value of $w_l$ and $w_r$, for deriving the one or more sets of hierarchical extremas, wherein the Vis represented as $T_p=w_l+w_r$, the $T_{st}$ is represented as $T_{st}=w_p/2$ and the $T_t$ is represented as $T_t=(w_l+w_r)/4$;
identify, one or more elements of signal patterns, based upon the one or more sets of hierarchical extremas, wherein the one or more elements of signal patterns comprise multiple frequencies and significance associated with the cardiovascular signal for defining a plurality of physiological events of the user or noise, wherein identifying the significance of the one or more elements of the signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal;

detect, the anomaly in the cardiovascular signal by:
determining occurrences of the one or more elements of signal patterns;
determine randomness of occurrences of the one or more elements of signal patterns, by computing an entropy of occurrences of the one or more elements of signal patterns, wherein the entropy comprises randomness of the one or more elements of signal patterns computed based upon probabilities of repetitions of the one or more elements of signal patterns, and wherein determining the randomness of occurrences of the one or more elements of signal patterns comprises obtaining one or more threshold values based upon an equi-probable occurrence of the one or more elements of signal patterns for classifying the one or more elements of signal patterns; and
identify, significance of repetitions of the one or more elements of signal patterns, based upon the occurrences and randomness of occurrences to detect the anomaly in the cardiovascular signal, wherein identifying the significance of repetitions of the one or more elements of signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal.

7. The system of claim 6, wherein the one or more hardware processors are further configured to identify the significance of the one or more elements of signal patterns by evaluating entropy of elements of a lower triangular matrix based upon frequencies and number of points in the one or more elements of signal patterns to detect randomness of the one or more elements of signal patterns.

8. The system of claim 6, wherein the one or more hardware processors are further configured to:
(iii) detect, one or more zero patterns in the cardiovascular signal based upon the one or more sets of hierarchical extremas; and
(iv) filter, the one or more zero patterns, based upon a comparison of the one or more zero patterns and a predefined threshold for identifying the one or more elements of signal patterns to detect the anomaly in the cardiovascular signal.

9. The system of claim 6, wherein the one or more hardware processors are further configured to identify the one or more elements of signal patterns by identifying uni-modal and multi-modal patterns in the cardiovascular signal based upon the occurrences of the one or more elements of signal patterns to detect the anomaly.

10. The system of claim 6, wherein the one or more hardware processors are further configured to obtain the one or more threshold values by computing an upper threshold value based upon occurrences and henceforth entropy of the one or more elements of signal patterns to detect the anomaly.

11. One or more non-transitory machine readable information storage mediums comprising one or more instructions which when executed by one or more hardware processors causes the one or more hardware processor to perform a method for detecting an anomaly in a cardiovascular signal using hierarchical extremas and repetitions, said method comprising:

smoothening, using a filter, the cardiovascular signal acquired for filtering the cardiovascular signal;

deriving, using a window detection technique, one or more sets of hierarchical extremas, based upon the smoothened cardiovascular signal, wherein the one or more sets of hierarchical extremas comprises maximum points and minimum points based on rising edges and falling edges of the cardiovascular signal, wherein each level of hierarchy in the one or more sets of hierarchical extremas represents a different window size of detection, and wherein the window detection technique to derive the one or more sets of hierarchical extremas comprising the steps of:
deriving a number of sampling points and amplitude difference from minima to maxima and maxima to minima;
performing clustering on the number of sampling points and the amplitude difference from the minima to maxima using k-means clustering to derive a number of clusters with centroids;
performing clustering on the number of sampling points and the amplitude difference from the maxima to minima using the k-means clustering to derive a number of clusters with centroids;
determining a plurality of boundaries of the number of clusters for the minima to maxima;
determining a plurality of boundaries of the number of clusters for the maxima to minima;
obtaining a value of window left ($w_l$) as a function of the plurality of boundaries of the number of clusters corresponding to the number of sampling points and the amplitude difference from the minima to maxima;
obtaining a value of window right ($w_r$) as a function of the plurality of boundaries of the number of clusters corresponding to the number of sampling points and the amplitude difference from the maxima to minima; and
obtaining a primary window ($T_p$), a secondary window ($T_{st}$) and a tertiary window ($T_t$) using the obtained value of $w_l$ and $w_r$, for deriving the one or more sets of hierarchical extremas, wherein the $T_p$ represented as $T_p=w_l+w_r$, the $T_{st}$ is represented as $T_{st}=w_l/2$ and the $T_t$ is represented as $T_t=(w_l+w_r)/4$;

identifying, one or more elements of signal patterns, based upon the one or more sets of hierarchical extremas, wherein the one or more elements of signal patterns comprise multiple frequencies and significance associated with the cardiovascular signal for defining a plurality of physiological events of the user or noise, wherein identifying the significance of the one or more elements of the signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal;

detecting, the anomaly in the cardiovascular signal by:
  determining occurrences of the one or more elements of signal patterns;
  determining randomness of occurrences of the one or more elements of signal patterns, by computing an entropy of occurrences of the one or more elements of signal patterns, wherein the entropy comprises randomness of the one or more elements of signal patterns computed based upon probabilities of repetitions of the one or more elements of signal patterns, and wherein determining the randomness of occurrences of the one or more elements of signal patterns comprises obtaining one or more threshold values based upon an equi-probable occurrence of the one or more elements of signal patterns for classifying the one or more elements of signal patterns; and
  identifying, significance of repetitions of the one or more elements of signal patterns, based upon the occurrences and randomness of occurrences to detect the anomaly in the cardiovascular signal, wherein identifying the significance of repetitions of the one or more elements of signal patterns comprises obtaining a lower triangular matrix based upon the one or more sets of hierarchy of extremas, and wherein the lower triangular matrix comprises number of occurrences of the one or more elements of signal patterns to identify variability in the cardiovascular signal.

* * * * *